(12) United States Patent
Sinderby et al.

(10) Patent No.: US 8,485,980 B2
(45) Date of Patent: Jul. 16, 2013

(54) ELECTRODE POSITIONING

(75) Inventors: Christer Sinderby, Toronto (CA); Jennifer Beck, Toronto (CA); Fredrik Jalde, Bromma (SE); Joachim Sallvin, Saltsjö-Boo (SE)

(73) Assignee: Maquet Critical Care AB, Solna (SE)

( * ) Notice: Subject to any disclaimer, the term of this patent is extended or adjusted under 35 U.S.C. 154(b) by 1048 days.

(21) Appl. No.: 12/239,134

(22) Filed: Sep. 26, 2008

(65) Prior Publication Data

US 2009/0137911 A1    May 28, 2009

Related U.S. Application Data

(60) Provisional application No. 60/960,430, filed on Sep. 28, 2007.

(30) Foreign Application Priority Data

Sep. 28, 2007  (SE) .................................... 0702191-8

(51) Int. Cl.
*A61B 5/08*        (2006.01)
*A61B 5/042*       (2006.01)

(52) U.S. Cl.
USPC ........................... 600/484; 600/513; 607/124

(58) Field of Classification Search
USPC .................... 600/509, 484, 513, 380; 607/40, 607/133, 124
See application file for complete search history.

(56) References Cited

U.S. PATENT DOCUMENTS

| 5,048,532 A | 9/1991 | Hickey |
| 5,671,752 A | 9/1997 | Sinderby et al. |

(Continued)

FOREIGN PATENT DOCUMENTS

| WO | WO 2005048839 A1 * | 6/2005 |
| WO | 2005/115234 | 12/2005 |
| WO | 2006/049787 | 5/2006 |

OTHER PUBLICATIONS

Allo et al., "Influence of Neurally Adjusted Ventilatory Assist and Positive End-Expiratory Pressure on Breathing Pattern in Rabbits with Acute Lung Injury", Crit Care Med 34, pp. 29997-3004, 2006.

(Continued)

*Primary Examiner* — Tammie K Heller
(74) *Attorney, Agent, or Firm* — Fay Kaplun & Marcin, LLP

(57) ABSTRACT

In a method and device for positioning a linear array of electrodes mounted on a distal end section of an elongated flexible member in a patient's respiratory airways at the level of the patient's diaphragm, a length of the elongated flexible member pre-determined to position the linear array of electrodes at the level of the patient's diaphragm is inserted through the patient's respiratory airways. Signals representative of an electrical activity of the patient's diaphragm (EAdi) are detected through the electrodes of the linear array, a presence or absence of ECG signal components is detected in the EAdi signals, and the position of the linear array of electrodes in the patient's respiratory airways is detected in response to the presence or absence of the ECG signal components in the EAdi signals. Also, lower esophageal sphincter activity may be detected in the EAdi signals, and the position of the linear array of electrodes in the patient's respiratory airways determined in response to the detected lower esophageal sphincter. Finally, an end-expiratory occlusion of the patient's respiratory airways may be performed to verify that the electrical activity of the diaphragm coincides with a negative deflection of the patient's respiratory airways pressure again in view of determining adequate positioning of the linear array of electrodes.

35 Claims, 15 Drawing Sheets

U.S. PATENT DOCUMENTS

| | | | |
|---|---|---|---|
| 5,820,560 | A | 10/1998 | Sinderby et al. |
| 6,259,938 | B1 | 7/2001 | Zarychta et al. |
| 6,584,347 | B1 | 6/2003 | Sinderby |
| 6,588,423 | B1 | 7/2003 | Sinderby |
| 7,021,310 | B1* | 4/2006 | Sinderby et al. ......... 128/204.23 |
| 7,273,056 | B2 | 9/2007 | Wilson et al. |
| 2004/0230110 | A1 | 11/2004 | Sinderby |
| 2005/0159659 | A1* | 7/2005 | Sawan et al. .................. 600/380 |
| 2010/0180896 | A1* | 7/2010 | Blomquist et al. ....... 128/204.23 |

OTHER PUBLICATIONS

Beck et al., "Improved Synchrony and Respiratory Unloading by Neurally Adjusted Ventilatory Assist (NAVA) in Lung-Injurred Rabbits", Pediatric Research 61, pp. 289-294, 2007.

Beck et al., "Influence of Bipolar Esophageal Electrode Positioning on Measurements of Human Crural Diaphragm Electromyogram", J Appl Physiol 81, pp. 1434-1449, 1996.

Sinderby et al. "Inspiratory Unloading by Neurally Adjusted Ventilatory Assist During Maximal Inspiratory Efforts in Healthy Subjects", Chest 131, pp. 711-717, 2007.

Sinderby et al., "Neural Control of Mechanical Ventilation in Respiratory Failure", Nat. Med 5, pp. 1433-1436, 1999.

Sinderby et al., "Enhancement of Signal Quality in Espohageal Recordings of Diaphragm" EMG Appl Physiol 82, pp. 1370-1377, 1997.

Beckstand et al., "Predicting Internal Distance to the Stomach for Positioning Nastogastric and Orogastric Feeding Tubes in Children", Journal of Advanced Nursing, vol. 59, No. 3, pp. 274-289, Aug. 2007.

\* cited by examiner

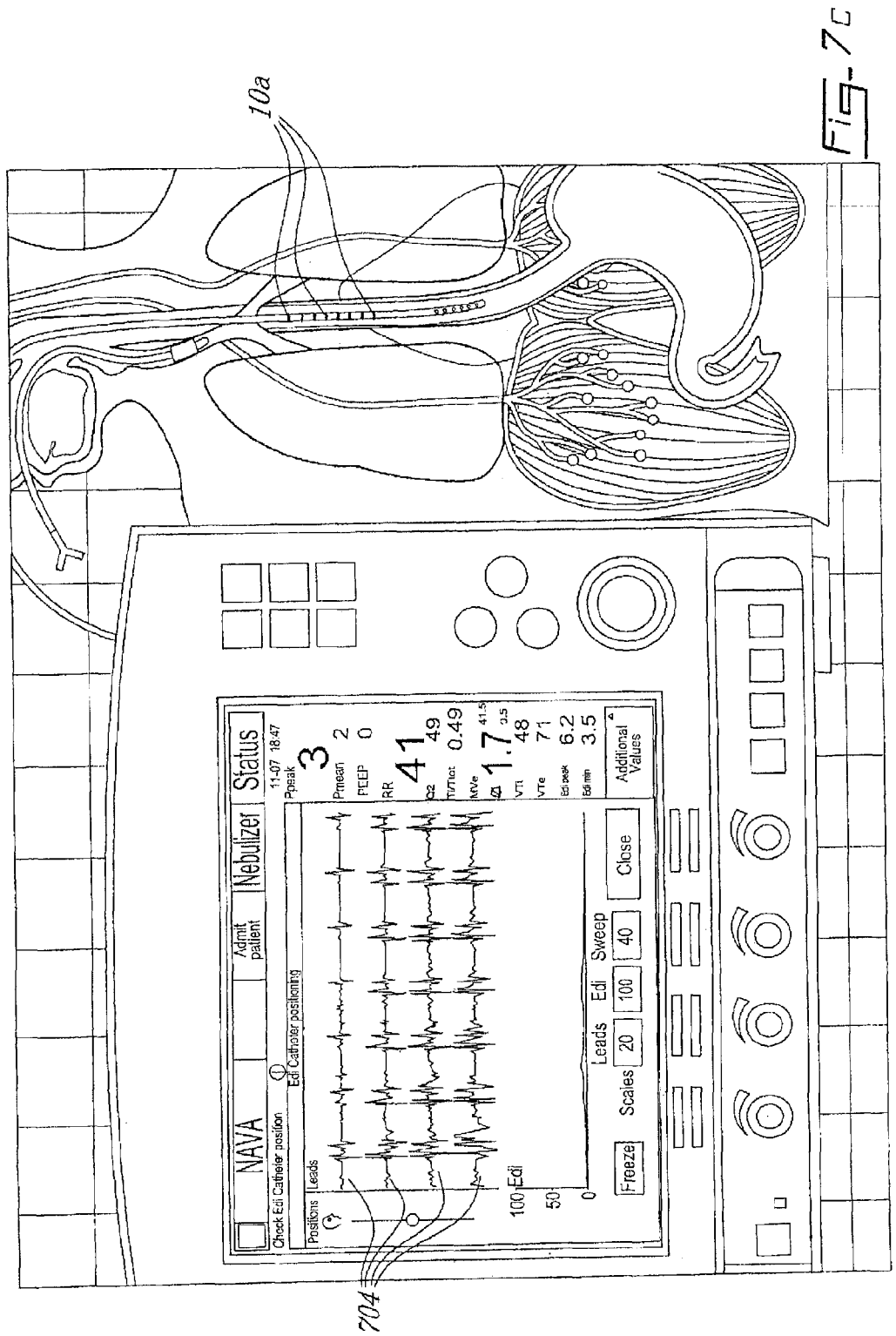

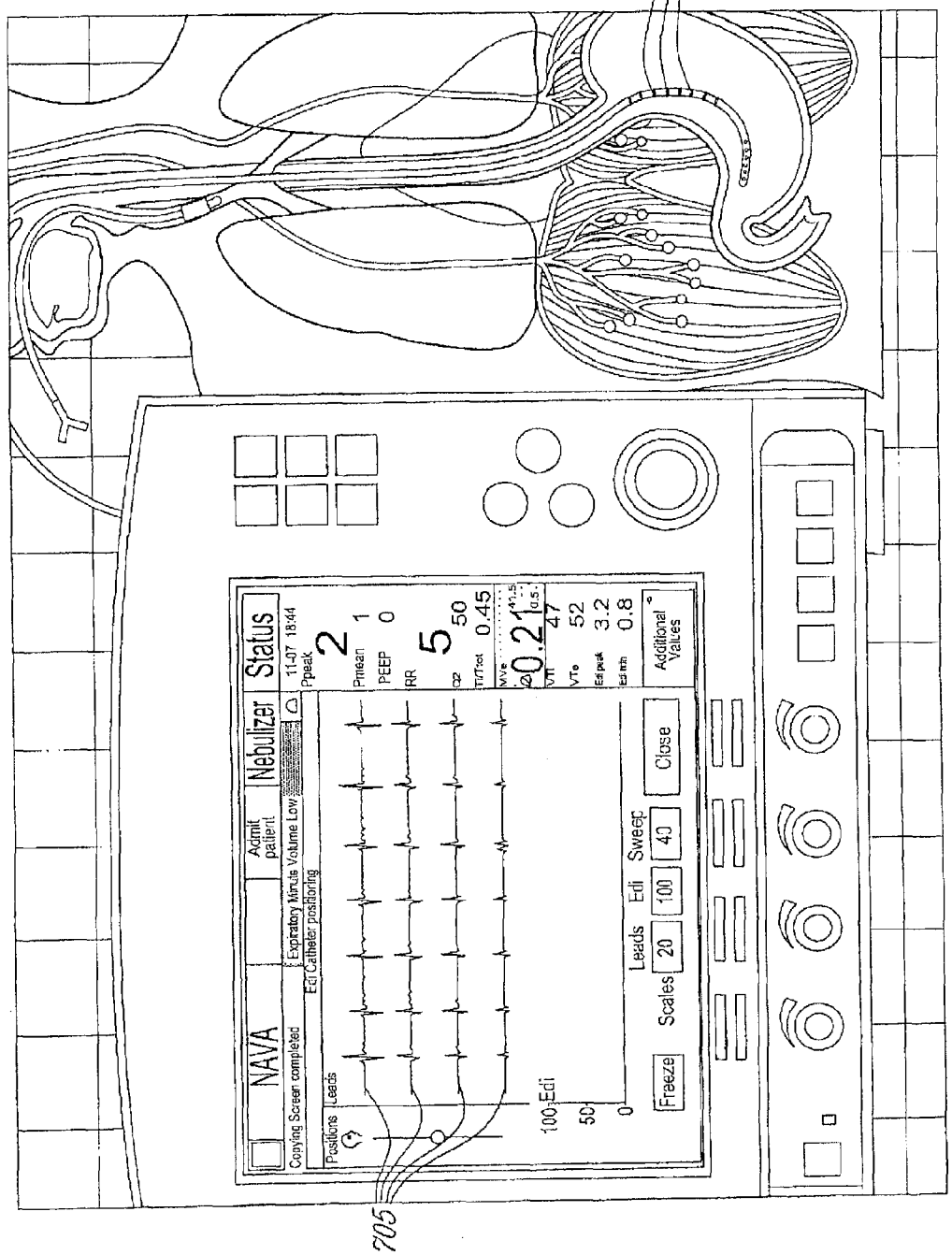

ELECTRODE POSITIONING

PRIORITY CLAIM

This application claims the benefit of U.S. Provisional Patent Application Ser. No. 60/960,430 filed on Sep. 28, 2007 and Swedish patent Application No. SE 0702191-8 filed on Sep. 28, 2007, the specifications of which are expressly incorporated herein, in their entirety, by reference.

FIELD

The present invention generally relates to ventilatory assist. More specifically, the present invention is concerned with a method and device for positioning a linear array of electrodes in view of measuring the electrical activity of a respiratory muscle, for example the diaphragm.

BACKGROUND

Neurally Adjusted Ventilatory Assist (NAVA) uses the electrical activity of the patient's diaphragm (EAdi) to trigger and cycle-off the pressure delivered to the patient's respiratory airways (Paw), as well as to adjust this pressure Paw in proportion to the electrical activity EAdi throughout patient's inspiration (Sinderby et al. [5]). The electrical activity EAdi of the patient's diaphragm is representative of the patient's respiratory drive and is influenced by facilitatory and inhibitory feedback loops that integrate information from mechano- and chemo-receptors as well as voluntary and behavioral inputs (Allo et al. [1]; Sinderby et al. [4]). With NAVA, the electrical activity EAdi of the patient's diaphragm simultaneously controls the diaphragm and the ventilator which hence conceptually acts as an external "respiratory muscle". Studies in animals and healthy human volunteers show that NAVA efficiently unloads the respiratory muscles, prevents excessive lung distension (Sinderby et al. [4]; Beck et al. [2]; Allo et al. [1]) and improves patient-ventilator synchrony (Beck et al. [2]). NAVA is described in U.S. Pat. No. 5,820,560 (Sinderby et al.) entitled "Inspiratory Proportional Pressure Assist Ventilation Controlled by a Diaphragm Electromyographic Signal" and in U.S. Pat. No. 6,588,423 (Synderby) entitled "Method and Device Responsive to Myoelectrical Activity for Triggering Ventilatory Support".

The electrical activity EAdi of the patient's diaphragm is derived from a linear array of electrodes such as 10 (FIG. 1) and a reference electrode (not shown) mounted on the distal end section of a naso-gastric feeding esophageal catheter 11. The esophageal catheter 11 consists of a multiple lumen esophageal catheter. The electrodes 10 can be formed by wrapping a wire at least one turn around the catheter 11 after having removed the insulation from the wire. The esophageal catheter 11 and the linear array of electrodes 10 are then coated with hydrophilic medical grade polyurethane (not shown), providing a conductive and slippery surface covering the electrodes 10. This slippery surface eases insertion of the esophageal catheter 11 through the mouth or a nostril and then through the esophagus until the linear array of electrodes reaches the patient's diaphragm and reduces friction between the catheter/electrodes and patient's mucosa. All the EAdi signals such as 12 are differentially recorded. More specifically, as depicted in FIG. 1, the signal 13 between the first and second electrodes (electrode pair 1), the signal 14 between the second and third electrodes (electrode pair 2), the signal 15 between the third and fourth electrodes (electrode pair 3), and so on (until electrode pair 7 in the example of FIG. 1) are recorded. As illustrated in FIG. 1, all the EAdi signals 12 can be summed to enable an ECG trigger to detect patient's ECG (see signal 16 at the top of FIG. 1 and U.S. Pat. No. 5,671,752 (Sinderby et al.) entitled "Diaphragm Electromyography Analysis Method and System").

As shown in FIG. 2, a cross-correlation algorithm (see curve 20) is used to determine the most negatively correlated pairs of electrodes 10. The EAdi signals from these most negatively correlated pairs of electrodes 10 are assumed to represent the electrical activity EAdi of the patient's diaphragm when the linear array of electrodes 10 passes through the diaphragm and is substantially centered about the patient's diaphragm (see U.S. Pat. No. 6,584,347 (Sinderby) entitled "Disturbance-Free Electromyographic Probe"; Published U.S. Patent Application 2004/0230110 A1 (Sinderby et al.) entitled "Control of Inter-Electrode Resistivity to Improve Quality of Measured Electrical Biological Signals"; Beck et al. [3]; and Sinderby et al. [6]).

In brief, the human crural diaphragm forms a few centimeter thick muscular tunnel around the esophagus, where the muscle fibers run mostly perpendicular to the esophageal catheter 11. The diaphragm around the esophagus defines an electrically active region (EARdi) during contractions. The linear array of electrodes 10 within the esophagus is oriented perpendicular to this region. As illustrated by the curve 20 of FIG. 2, EAdi signals measured simultaneously via pairs of electrodes 10 (among electrode pairs 1-7) positioned on the same side of the diaphragm have a correlation coefficient close to +1, whereas EAdi signals measured via pairs of electrodes 10 on opposite sides of the diaphragm have a correlation coefficient close to −1. Such cross-correlation analyses are performed between segments of non-processed differentially recorded EAdi signals obtained via the seven pairs 1-7 of electrodes 10. The most negative correlation coefficient between any two pairs of electrodes (between electrode pairs 3 and 5 in the example of FIG. 2) indicates that the respective EAdi signals are the most reversed in polarity. The electrode(s) 10 located between these two most negatively correlated pairs is(are) the electrode(s) closest to the center of the EARdi region.

In order to effectively detect the electrical activity EAdi of the Patient's diaphragm, the array of electrodes on the distal end section of the esophageal catheter must be adequately positioned at the level of the diaphragm. This position will also allow the linear array of electrodes 10 to cover the inspiratory and expiratory displacement of the diaphragm.

However, a problem when detecting electrical activity EAdi of the Patient's diaphragm is positioning of the catheter within the patient's oesophagus. To obtain proper EAdi signals some of the electrodes of the linear array should be placed above the diaphragm and some below the patient's diaphragm. There is a possibility that the esophageal catheter 11 will be inserted too far, or not be inserted far enough. In both cases the array of electrodes 10 mounted on the distal end section of the esophageal catheter 11 will detect either weak EAdi signals or even may not capture any signal at all. The esophageal catheter 11 may also capture myoelectrical signals from other muscles instead of, or in addition to, the EAdi signals from the patient's diaphragm. Hence, there is a need for an improved method and device for appropriately positioning a linear array of electrodes mounted on a distal end section of an esophageal catheter in a patient's respiratory airways at the level of the patient's diaphragm.

SUMMARY

According to the present invention, there is provided a method for positioning a linear array of electrodes mounted on a distal end section of an elongated flexible member in a patient's respiratory airways at the level of the patient's diaphragm, comprising: inserting through the patient's respiratory airways a length of the elongated flexible member pre-determined to position the linear array of electrodes at the level of the patient's diaphragm; detecting through the electrodes of the linear array signals representative of an electrical activity of the patient's diaphragm (EAdi); detecting ECG signal components in the EAdi signals; and detecting the position of the linear array of electrodes in the patient's respiratory airways in response to the detected ECG signal components in the EAdi signals.

The present invention also relates to a method for positioning a linear array of electrodes mounted on a distal end section of an elongated flexible member in a patient's respiratory airways at the level of the patient's diaphragm, comprising: inserting through the patient's respiratory airways a length of the elongated flexible member pre-determined to position the linear array of electrodes at the level of the patient's diaphragm; detecting through the electrodes of the linear array signals representative of an electrical activity of the patient's diaphragm (EAdi); detecting lower esophageal sphincter activity in the EAdi signals; and detecting the position of the linear array of electrodes in the patient's respiratory airways in response to the detected lower esophageal sphincter activity.

According to the present invention, there is also provided a device for positioning a linear array of electrodes mounted on a distal end section of an elongated flexible member in a patient's respiratory airways at the level of the patient's diaphragm, wherein a length of the elongated flexible member pre-determined to position the linear array of electrodes at the level of the patient's diaphragm is first inserted through the patient's respiratory airways and wherein the device comprises: means for detecting through the electrodes of the linear array signals representative of an electrical activity of the patient's diaphragm (EAdi); means for detecting ECG signal components in the EAdi signals; and means for detecting the position of the linear array of electrodes in the patient's respiratory airways in response to the detected ECG signal components in the EAdi signals.

The present invention further relates to a device for positioning a linear array of electrodes mounted on a distal end section of an elongated flexible member in a patient's respiratory airways at the level of the patient's diaphragm, wherein a length of the elongated flexible member pre-determined to position the linear array of electrodes at the level of the patient's diaphragm is first inserted through the patient's respiratory airways and wherein the device comprises: a first detector of signals representative of an electrical activity of the patient's diaphragm (EAdi) through the electrodes of the linear array; a second detector of ECG signal components in the EAdi signals; and a third detector of the position of the linear array of electrodes in the patient's respiratory airways in response to the detected ECG signal components in the EAdi signals.

According to the present invention there is further provided a device for positioning a linear array of electrodes mounted on a distal end section of an elongated flexible member in a patient's respiratory airways at the level of the patient's diaphragm, wherein a length of the elongated flexible member pre-determined to position the linear array of electrodes at the level of the patient's diaphragm is first inserted through the patient's respiratory airways and wherein the device comprises: means for detecting signals representative of an electrical activity of the patient's diaphragm (EAdi) through the electrodes of the linear array; means for detecting lower esophageal sphincter activity in the EAdi signals; and means for detecting the position of the linear array of electrodes in the patient's respiratory airways in response to the detected lower esophageal sphincter activity.

The present invention still further relates to a device for positioning a linear array of electrodes mounted on a distal end section of an elongated flexible member in a patient's respiratory airways at the level of the patient's diaphragm, wherein a length of the elongated flexible member pre-determined to position the linear array of electrodes at the level of the patient's diaphragm is first inserted through the patient's respiratory airways and wherein the device comprises: a first detector of signals representative of an electrical activity of the patient's diaphragm (EAdi) through the electrodes of the linear array; a second detector of lower esophageal sphincter activity in the EAdi signals; and a third detector of the position of the linear array of electrodes in the patient's respiratory airways in response to the detected lower esophageal sphincter activity.

Also in accordance with the present invention, there is provided a method for positioning a linear array of electrodes mounted on a distal end section of an elongated flexible member in a patient's respiratory airways at the level of the patient's diaphragm, comprising:

in a first operation:
  inserting through the patient's respiratory airways a length of the elongated flexible member pre-determined to position the linear array of electrodes at the level of the patient's diaphragm;

in a second operation:
  detecting through the electrodes of the linear array signals representative of an electrical activity of the patient's diaphragm (EAdi);
  detecting ECG signal components in the EAdi signals; and
  a first detection of the position of the linear array of electrodes in the Patient's respiratory airways in response to detection of ECG signal components in the EAdi signals;

in a third operation:
  detecting lower esophageal sphincter activity in the EAdi signals; and
  a second detection of the position of the linear array of electrodes in the Patient's respiratory airways in response to the detected lower esophageal sphincter activity; and in a fourth operation:
  performing an end-expiratory occlusion of the patient's respiratory airways;
  verifying during the end-expiratory occlusion that the electrical activity of the diaphragm coincides with a negative deflection of the patient's respiratory airways pressure; and
  a third detection of adequate positioning of the linear array of electrodes in the patient's respiratory airways when the electrical activity of the diaphragm coincides with a negative deflection of the patient's respiratory airways pressure during the end-expiratory occlusion.

The present invention also relates to a device for positioning a linear array of electrodes mounted on a distal end section of an elongated flexible member in a patient's respiratory airways at the level of the patient's diaphragm, wherein a length of the elongated flexible member pre-determined to position the linear array of electrodes at the level of the patient's diaphragm is first inserted through the patient's respiratory airways and wherein the device comprises:

a detector of signals representative of an electrical activity of the patient's diaphragm (EAdi) through the electrodes of the linear array;
a detector of ECG signal components in the EAdi signals; and a detector of the position of the linear array of electrodes in the patient's respiratory airways in response to detection of ECG signal components in the EAdi signals;
a detector of lower esophageal sphincter activity in the EAdi signals; and a detector of the position of the linear array of electrodes in the patient's respiratory airways in response to the detected lower esophageal sphincter activity; and
an occluder for performing an end-expiratory occlusion of the patient's respiratory airways; a detector, during the end-expiratory occlusion, that the electrical activity of the diaphragm coincides with a negative deflection of the patient's respiratory airways pressure; and a detector of adequate positioning of the linear array of electrodes in the patient's respiratory airways when the electrical activity of the diaphragm coincides with a negative deflection of the patient's respiratory airways pressure during the end-expiratory occlusion.

The foregoing and other objects, advantages and features of the present invention will become more apparent upon reading of the following non-restrictive description of illustrative embodiments thereof, given by way of example only with reference to the accompanying drawings.

BRIEF DESCRIPTION OF THE DRAWINGS

In the appended drawings:

FIG. 7c is a graph showing that the QRS complex disappears from the ECG signals when the corresponding pairs of electrodes approach the patient's upper respiratory airways;

FIG. 7d is a graph showing that the P-wave is absent from the ECG signals when the corresponding pairs of electrodes is inserted in the patient's stomach;

DETAILED DESCRIPTION

The present disclosure refers to a number of documents which are herein incorporated by reference in their entirety.

As mentioned in the foregoing description, adequate detection of the electrical activity EAdi of the patient's diaphragm is dependent on the position of the linear array of electrodes 10 mounted on the distal end section of the esophageal catheter 11 (elongated flexible member). Also, the linear array of electrodes 10 on the esophageal catheter 11 is advantageously positioned in such a manner that this linear array of electrodes covers the inspiratory and expiratory displacements of the diaphragm.

Therefore, the present disclosure describes a number of operations that have been developed to adequately position the linear array of electrodes 10 at the level of the patient's diaphragm.

Each operation performed by the method and device for positioning the linear array of electrodes 10 mounted on the distal end section of the esophageal catheter 11 in the patient's esophagus (patient's respiratory airways) at the level of the patient's diaphragm will now be described.

Anatomical Measures

Figure 5:
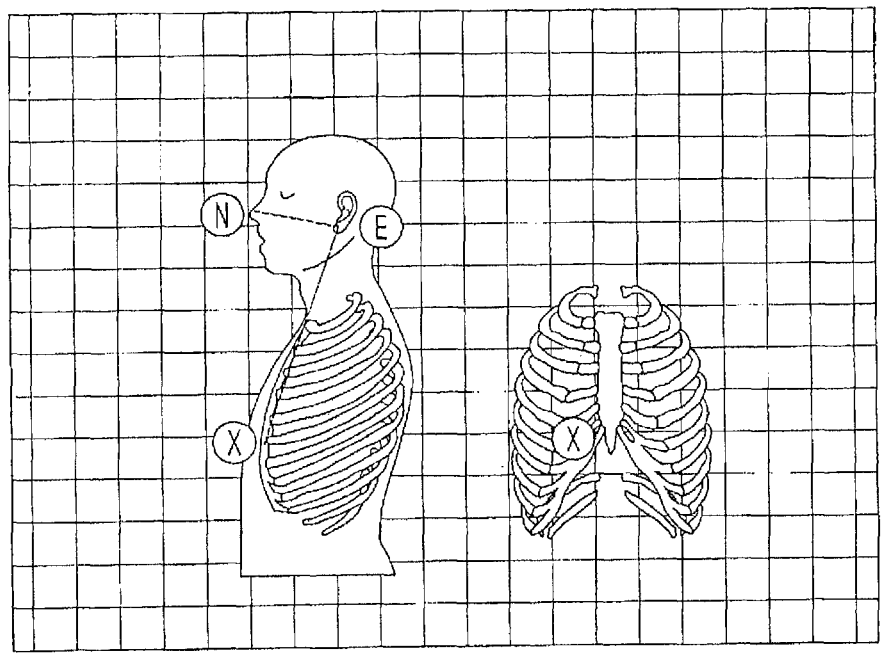
FIG. 5 is a schematic view showing the anatomical measurement of the nose-to-ear-to-xiphoid distance.
Figure 6:
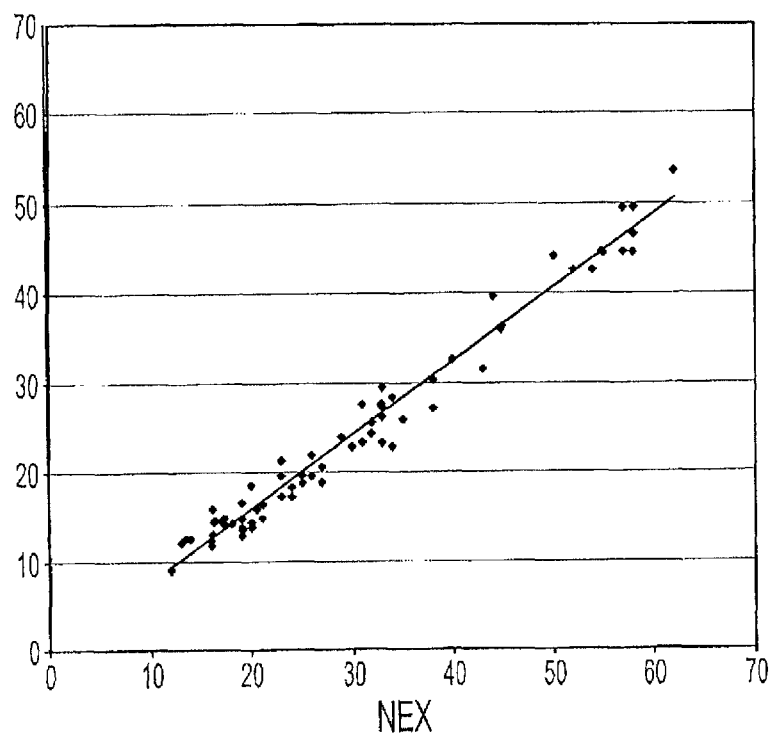
FIG. 6 is a graph of the nose-to-ear-to-xiphoid distance vs the distance from the nose to the center of the linear array of electrodes.

Anatomical measures provide the first landmark for positioning the linear array of electrodes 10 at the level where the esophagus passes through the patient's diaphragm. It has been found that the nose-to-ear-to-xiphoid distance (NEX distance in FIG. 5) is related to the distance inside the patient's body from the patient's nose or mouth to the diaphragm. For example, as depicted by the graph of FIG. 6, the length of esophageal catheter 11 to be inserted through the patient's nose to position the linear array of electrodes 10 at the level of the patient's diaphragm can be predicted or estimated, i.e. pre-calculated by multiplying the nose-to-ear-to-xiphoid distance by a regression coefficient of 0.82; the inserted length of esophageal catheter is determined from the center of the linear array of electrodes 10. With oral insertion of the esophageal catheter 11, the estimated length of esophageal catheter 11 is pre-calculated by multiplying the nose-to-ear-to-xiphoid distance by a regression coefficient of 0.74; again the inserted length of esophageal catheter is measured from the center of the linear array of electrodes 10.

Given this extremely strong correlation between anatomical measures and the distance through the patient's respiratory airways i.e. from the nose or mouth through the esophagus to the diaphragm, a first operation 301 (FIG. 3) in positioning of the linear array of electrodes 10 is to measure the nose-to-ear-to-xiphoid distance.

In operation 302 (FIG. 3), the measured nose-to-ear-to-xiphoid distance is input to a catheter length calculator 4011 of the catheter insertion monitoring system 401 (FIG. 4) along with an indication as to whether the catheter will be inserted through the patient's nose or mouth.

In operation 303, the catheter length calculator 4011 multiplies the measured nose-to-ear-to-xiphoid distance by the appropriate one of the above regression coefficients depending on whether the esophageal catheter 11 will be inserted through the patient's nose or mouth. The catheter insertion monitoring system 401 further comprises a display 4012 on which is displayed the length of esophageal catheter 11 to be inserted through the patient's nose or mouth as predicted or estimated, i.e. pre-calculated by multiplying the measured nose-to-ear-to-xiphoid distance by the appropriate regression coefficient.

In operation 304, the catheter insertion monitoring system 401 (FIG. 4) comprises a catheter insertion length monitor 4013 for monitoring the insertion of the esophageal catheter 11 through either the patient's nose or mouth. For that purpose, the catheter insertion length monitor 4013 may comprise a detector (not shown) for measuring the length of esophageal catheter 11 from the center of the linear array of electrodes 10 that has been inserted through the patient's nose or mouth through the esophagus (patient's respiratory airways) and the display 4012 will display this measured inserted catheter length. For example, the catheter length measuring detector can be any available optical, mechanical, electrical or video processing detector of linear displacement.

In operation 305, the esophageal catheter 11 is inserted and advanced though the mouth or nose and the esophagus (patient's respiratory airways) until the displayed, measured length of esophageal catheter 11 having been inserted through the patient's respiratory airways has reached the pre-calculated catheter length as indicated on the display of the catheter insertion monitoring system 401.

ECG Verification of the Position of the Array of Electrodes

Verification of adequate positioning of the array of electrodes 10 at the level of the patient's diaphragm is then performed to exclude inappropriate positioning should, for example, the esophageal catheter 11 be inserted into a lung.

Figure 1:
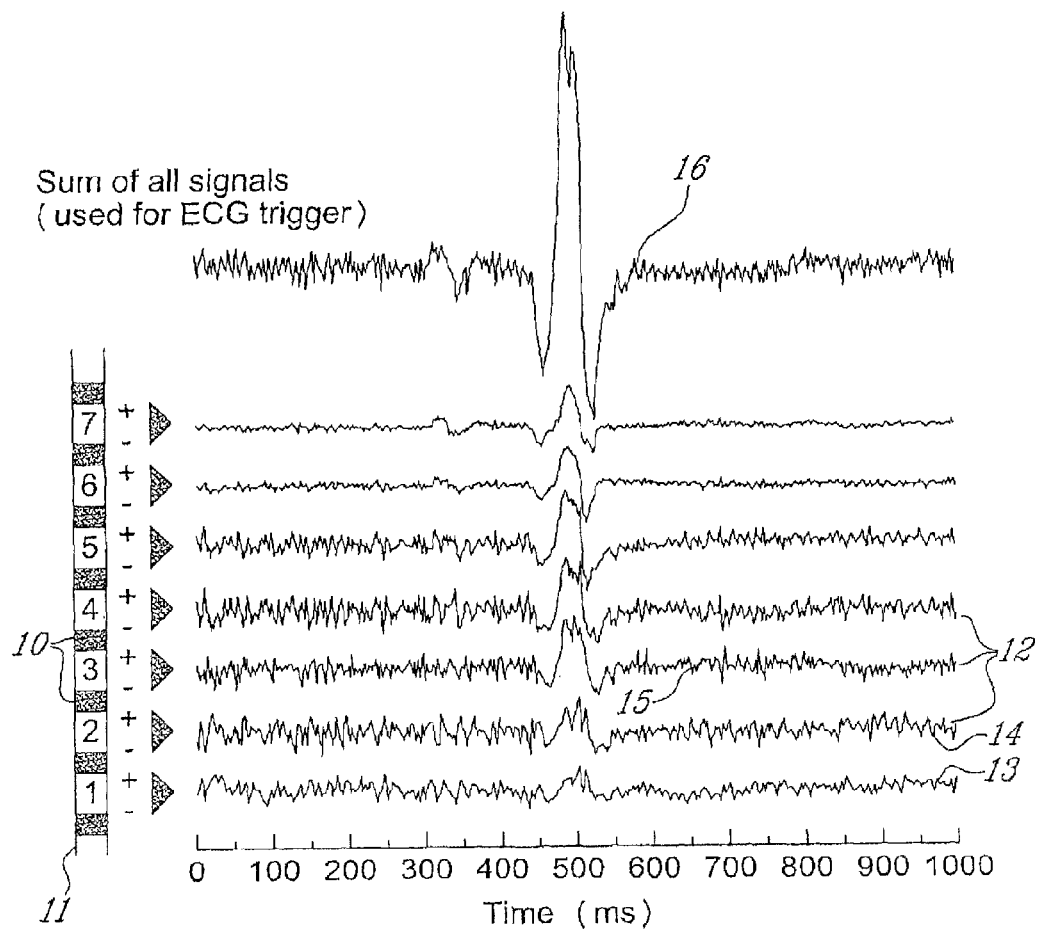
FIG. 1 is a graphical representation of an example of EAdi signals derived from a linear array of electrodes.
Figure 2:
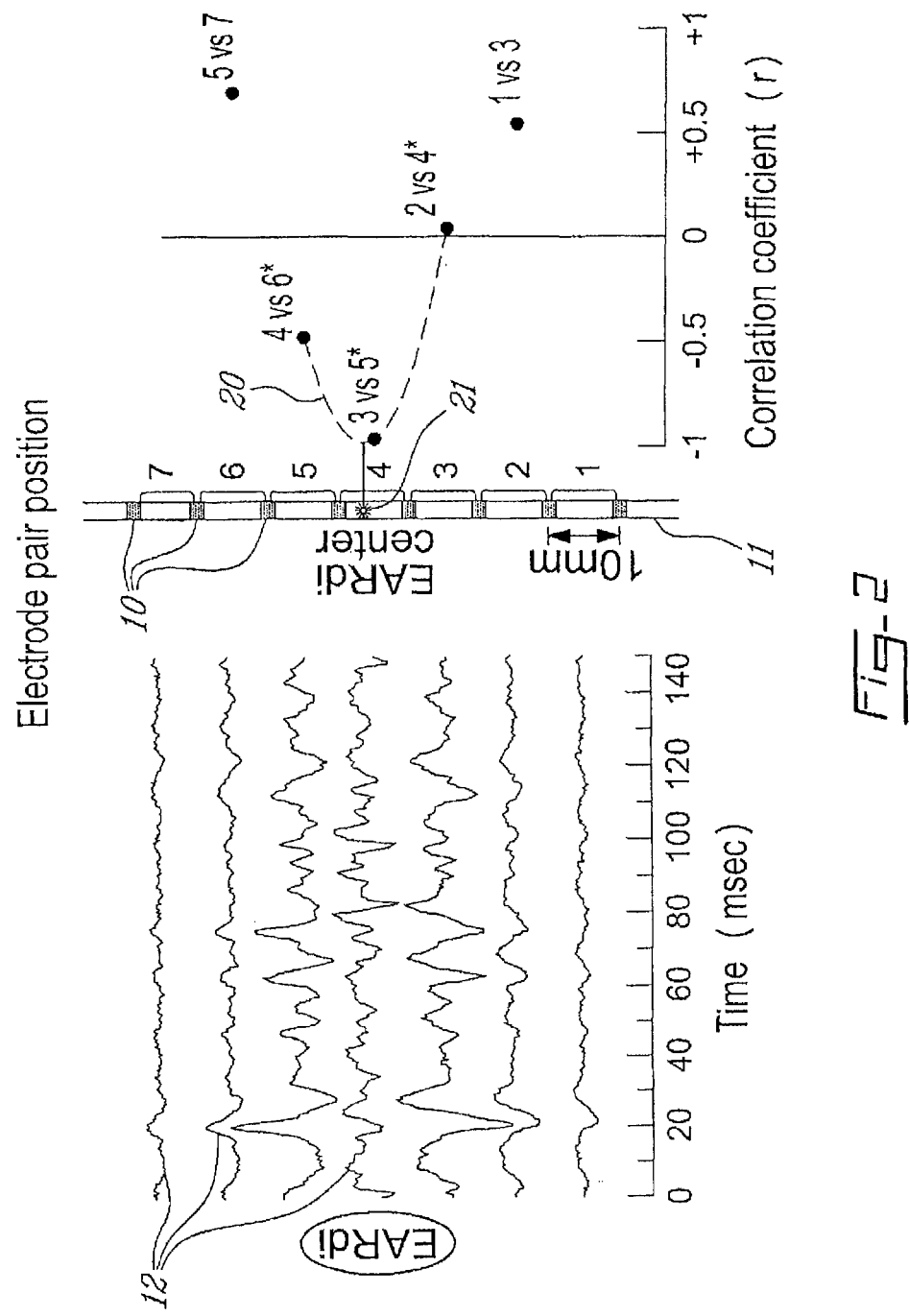
FIG. 2 is a graphical representation of an example of determination of the EARdi center via a cross-correlation algorithm.

This verification of the adequate positioning of the array of electrodes 10 can be performed by visual inspection of the raw EAdi signals (for example signals 12 in FIGS. 1 and 2) derived from each of the seven (7) pairs 1-7 of electrodes 10 (FIGS. 1 and 2).

The heart is positioned next to the esophagus with its base on the diaphragm. Even though the heart then becomes the most powerful source of cross-talk in the EAdi signals 12 (FIGS. 1 and 2), its anatomical features gives advantages in terms of verifying adequate positioning of the array of electrodes 10 at the level of the patient's diaphragm.

Figure 7A:
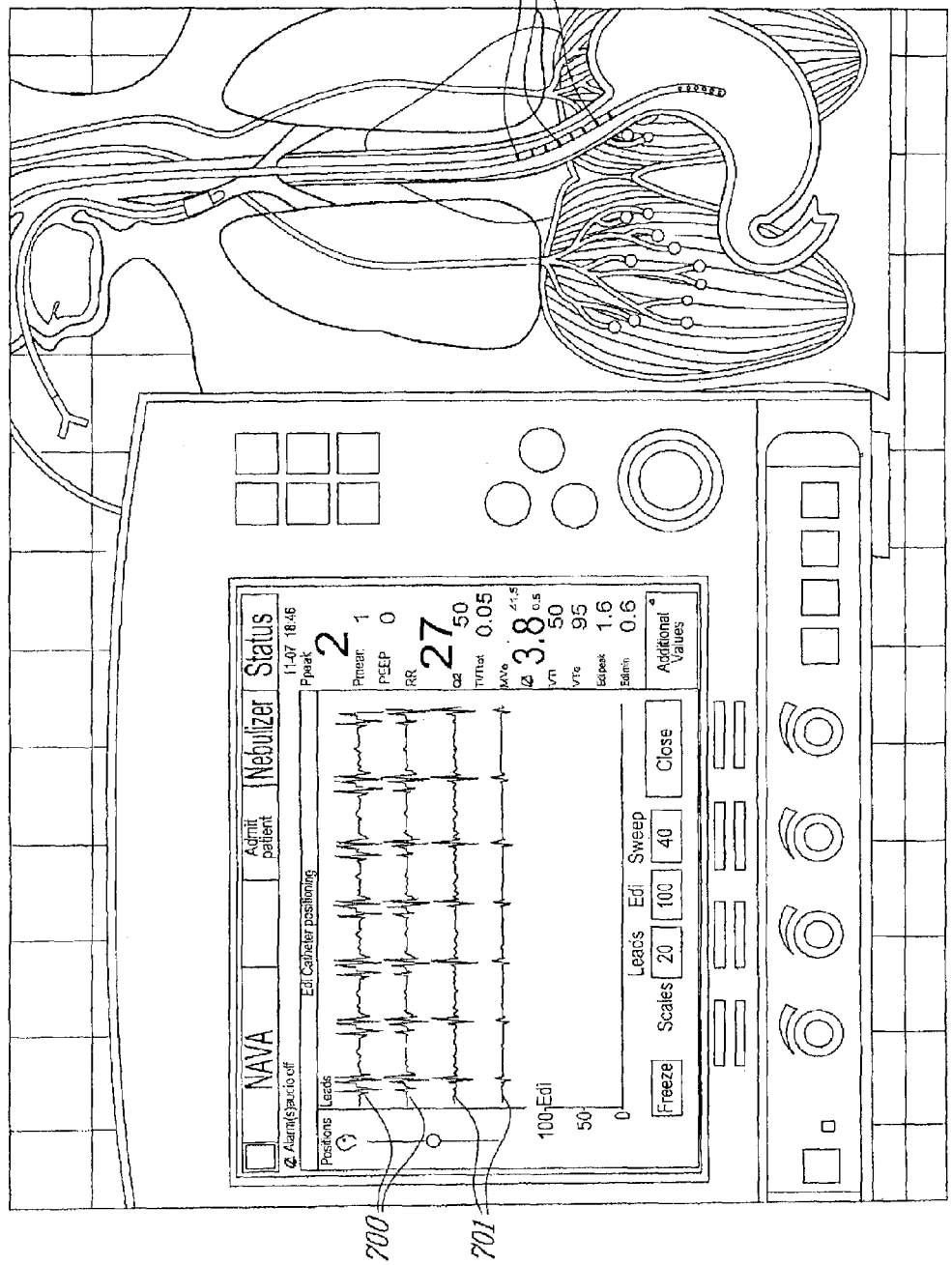
FIG. 7a is a graph showing that the ECG signal from the pairs of electrodes positioned above the diaphragm contains visible P-wave and QRS complex.
Figure 7B:
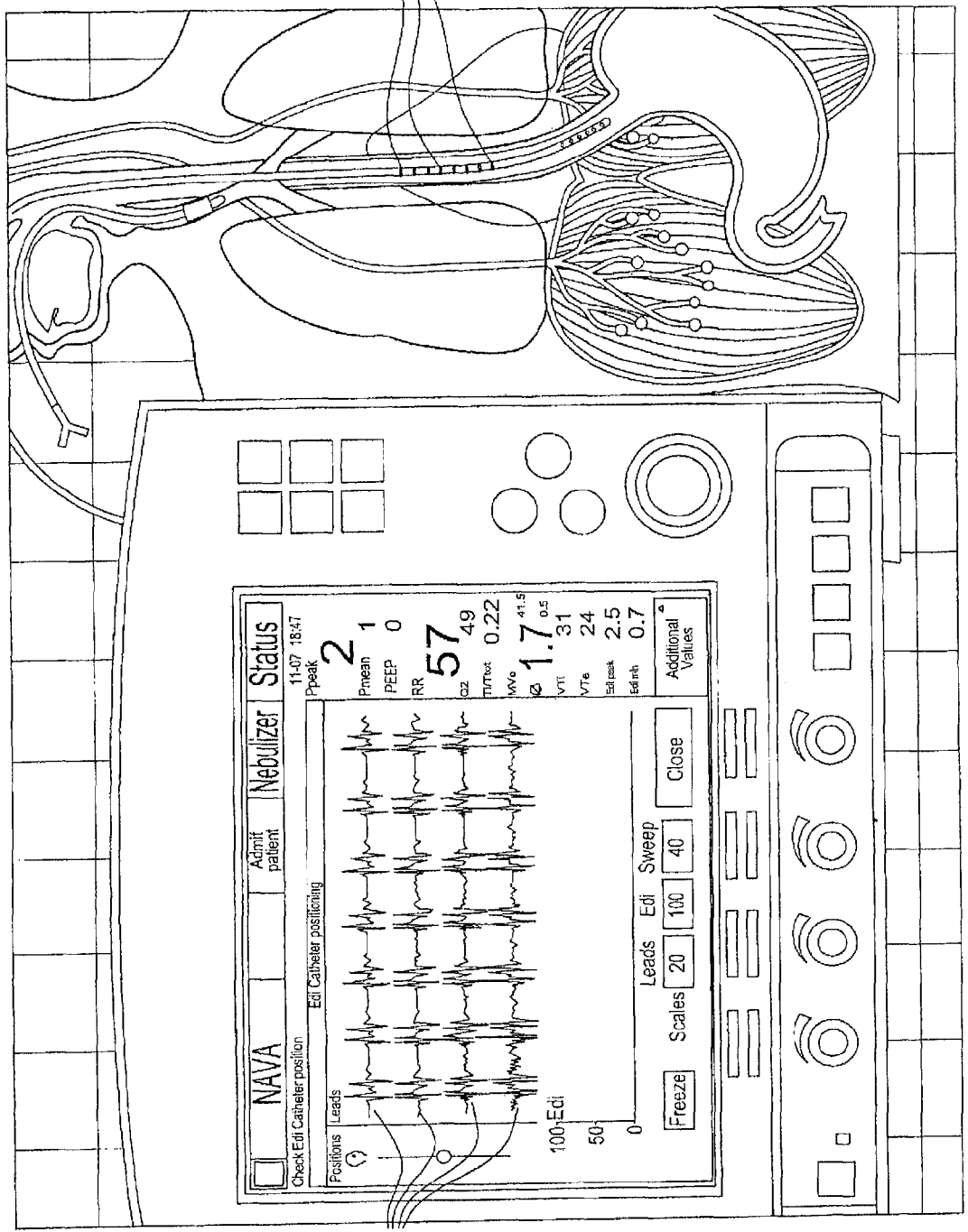
FIG. 7b is a graph showing that the ECG signals from all the pairs of electrodes contain a P-wave when the linear array of electrodes is positioned too far up in the esophagus.

Typically, an ECG signal component derived from the pairs of electrodes 10 above the diaphragm contains a clearly visible P-wave and a QRS complex as illustrated by the EAdi signals 700 of FIG. 7a. In the distal direction of the array of electrodes 10, the EAdi signals, for example the signals 701, that are obtained from pairs of electrodes below the patient's diaphragm and that approaches the stomach shows an absence of a P-wave and a lower-amplitude QRS complex (FIG. 7a). Also, when the array of electrodes 10 is positioned too far up in the esophagus all the channels (all the EAdi signals 703 from all the pairs of electrodes 10) show a P-wave and a QRS complex (FIG. 7b). When electrodes 10a of the linear array approach the upper portion of the patient's respiratory airways (FIG. 7c) the QRS complex disappears as shown by EAdi signals 704 in FIG. 7c. Finally, when the electrodes 10 of the linear array are inserted into the Patient's stomach, the P-wave is absent as illustrated by the EAdi signals 705 of FIG. 7d.

Therefore, a second landmark for adequate positioning of the linear array of electrodes 10 with respect to the diaphragm is derived through inspection of the ECG signal components contained in the EAdi signals. For that purpose, the following operations are conducted.

Figure 3:
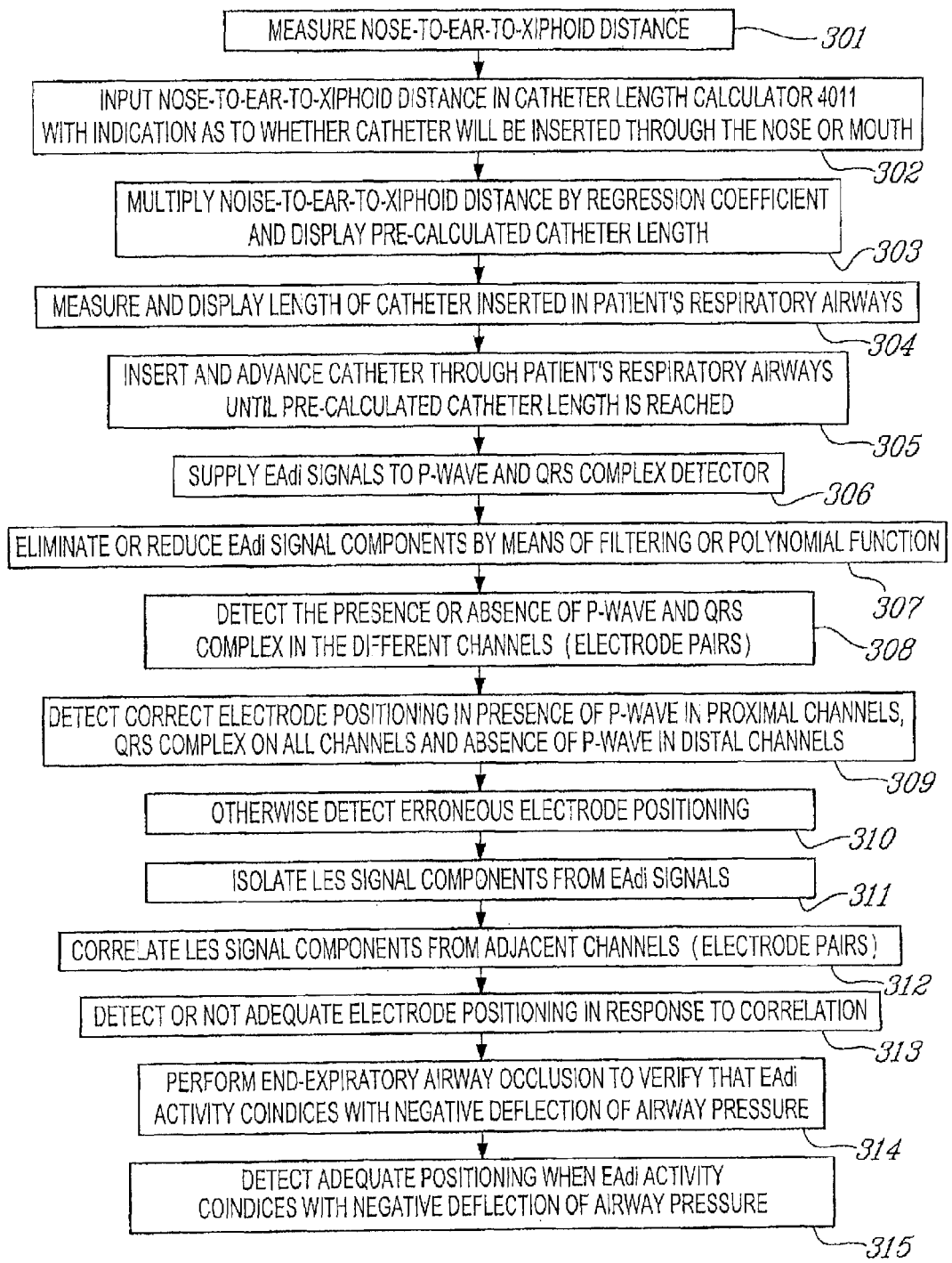
FIG. 3 is a flow chart of the operations of a non-restrictive illustrative embodiment of the method according to the invention, for positioning a linear array of electrodes in a patient's respiratory airways at the level of the patient's diaphragm.

In operation 306 of FIG. 3, a P-wave and QRS complex detector 402 (FIG. 4) is supplied with the EAdi signals 12 (FIGS. 1 and 2) from the electrode pairs 1-7 to detect the presence or absence of a P-wave and QRS complex components in the different EAdi signals 12.

For that purpose, in operation 307, the P-wave and QRS complex detector 402 first eliminates or reduces the EAdi signal components from the EAdi signals 12. The P-wave and QRS complex detector 402 comprises, to that effect, a band-pass filter 4021 for processing the EAdi signals 12 for the purpose of enhancing the ECG signal components while suppressing or attenuating the EAdi signal components. Alternatively, the P-wave and QRS complex detector 402 may comprise a processor 4022 for applying to the EAdi signals 12 a polynomial function enhancing the ECG signal components while suppressing or attenuating the EAdi signal components.

In operation 308, the P-wave and QRS complex detector 402 then detects in the output signals from the band-pass filter 4021 or polynomial function applying processor 4022 the presence or not of a P-wave and/or a QRS complex. Detection of ECG signal components on all channels (electrode pairs 1-7) quite simultaneously indicates the presence of a QRS complex on all channels. Also, if the QRS complex is preceded within a brief period of time by an amplitude appearing only on the most proximal channels (for example electrode pairs 5-7) of the array of electrodes 10, this is indicative of a P-wave on these most proximal pairs of electrodes 10.

In operation 309, detection by the P-wave and QRS complex detector 402 of (a) the presence of a P-wave on the most proximal channels (for example electrode pairs 5-7), i.e. close to the atrium, (b) the absence of a P-wave on the most distal channels (for example electrode pairs 1-3), i.e. in the stomach, and (c) the presence of a QRS complex on all the channels (electrode pairs 1-7) is indicative of adequate positioning of the array of electrodes 10 in the patient's respiratory airways at the level of the patient's diaphragm.

In Operation 310, detection by the P-wave and QRS complex detector 402 of the absence of the above pattern is indicative of erroneous positioning of the array of electrodes 10 with respect to the diaphragm or cardiac anomaly.

Another non-restrictive illustrative embodiment for verifying correct positioning of the array of electrodes 10 using the ECG will now be described in connection with FIGS. 10-12.

When the position of the linear array or electrodes 10 is approximately right each of the EAdi signals contains an ECG signal component since the electrodes 10 of the linear array will inevitably pick up the heart activity. Pairs of electrodes 10 that are positioned above the patient's diaphragm will detect a higher amplitude of the ECG signal than pairs of electrodes 10 that are positioned below the diaphragm, since the patient's diaphragm will cause a significant damping of the ECG signal amplitude.

The damping between the electrode pairs may be determined in a number of different ways. For example the difference between the peak-to-peak ECG signal amplitudes for each pair of electrodes 10 may be used. Alternatively the signal may be integrated to obtain the area, or the root mean square of the ECG signal at each pair of electrodes 10. The actual way of determining the damping is not essential.

When the P-wave amplitude is larger than the amplitude of the QRS complex, it may be necessary to separate the damping of the P-wave amplitude from the damping of the total ECG amplitude. The P-wave amplitude often decreases rapidly with the distance between the pair of electrodes 10 and the atrium. Thus a large reduction of amplitude may be detected above the patient's diaphragm and another large reduction of amplitude may be detected further down the linear array or electrodes 10 caused by the diaphragm. To distinguish the damping of the P-wave and the damping of the total ECG amplitude it is considered that the P-wave amplitude often decreases rapidly above the patient's diaphragm.

Starting at the lower end of the linear array or electrodes 10 it can be seen that a correctly placed linear array or electrodes 10 will have a low ECG signal amplitude on the pairs of electrodes 10 close to the stomach, a significant increase of the ECG signal amplitude at the pairs of electrodes 10 placed above the diaphragm, and then, in some cases, an additional increase of the ECG signal amplitude for the upper pairs of electrodes 10 placed close to the patient's atrium caused by a strong P-wave. However, in many cases the P-wave amplitude is non-existent, or minor, compared to the amplitude of the QRS complex.

The position of the diaphragm can be detected by measuring the EAdi signals through all the pairs of electrodes 10 continuously or within short time intervals, calculating the ECG signal amplitude on each pair of electrodes 10 and comparing the calculated ECG signal amplitudes from all the pairs of electrodes 10. Then the largest difference of ECG signal amplitude, damping, between at least two pairs of electrodes 10 is determined. The comparison between the pairs of electrodes 10 may, for example, be carried out according to the following procedure:

Starting at the lower end, the tip of the esophageal catheter 11, and going upwards along the linear array or electrodes 10:

Ascertain a relatively low ECG signal amplitude on the lower pair of electrodes 10;

Compare the ECG signal amplitudes of the lowest pair of electrodes 10 and second lowest pair of electrodes, then of the second and third lowest, and so on;

Determine the first significant increase of ECG signal amplitude along the linear array or electrodes 10.

Figure 10:
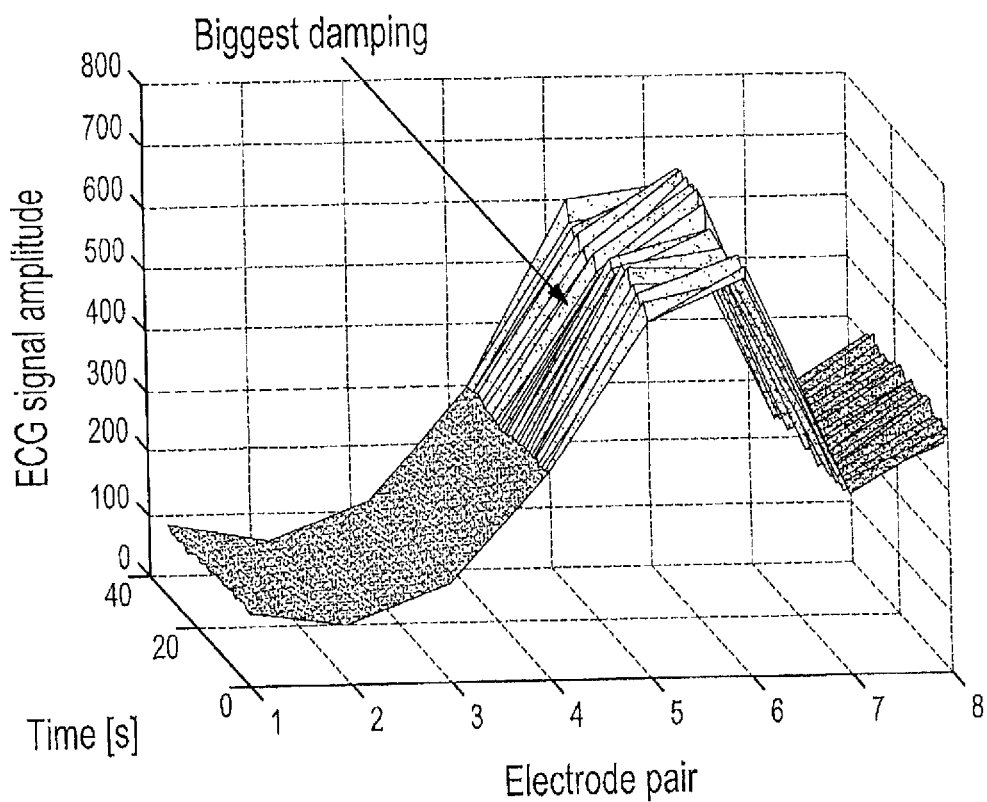
FIG. 10 is a graph illustrating the amplitude of the ECG signal as a function of time and electrode pairs.

The graph of FIG. 10 illustrates the variation in the ECG signal amplitude recorded by each of the pairs of electrodes 10. The electrode pairs are numbered 1-8 for a linear array of nine (9) electrodes, 1 being the pair formed by the two first electrodes 10 inserted into the patient, and 8 being the pair formed by the two last electrodes 10 inserted into the patient, that is, the uppermost pair of electrodes 10. As can be seen, the ECG signal amplitude varies between the pairs of electrodes 10. In the example of FIG. 10 the largest difference between two neighbouring pairs of electrodes 10 is found between pairs 4 and 5. Alternatively, the highest damping between combinations of three neighbouring pairs of electrodes 10 may be considered. It might be assumed that the amplitude should vary in the same direction between all pairs of electrodes 10, that is, that the amplitude recorded by electrode pair 1 should be higher than that of pair 2, which should in turn be higher than that of pair 3, etc. That this is not always the case is caused by other factors. For example, the P-wave, if present, might have an impact on the overall ECG signal amplitude.

The initial positioning of the linear array or electrodes 10 mounted on the distal end section of the esophageal catheter 11, before carrying out the method, should be made as precisely as possible using for example the above describe method. Advantageously, most of the electrodes 10 should be positioned below the diaphragm when starting the positioning of the linear array or electrodes 10 to avoid confusing the P-wave with the ECG signal. Therefore, it is recommended to use an estimated positioning method for the initial positioning. An examples of such method, using NEX, is discussed in the foregoing description.

In order to detect the right position a simple registration of the EAdi signals from all pairs of electrodes 10 may suffice.

Figure 11:
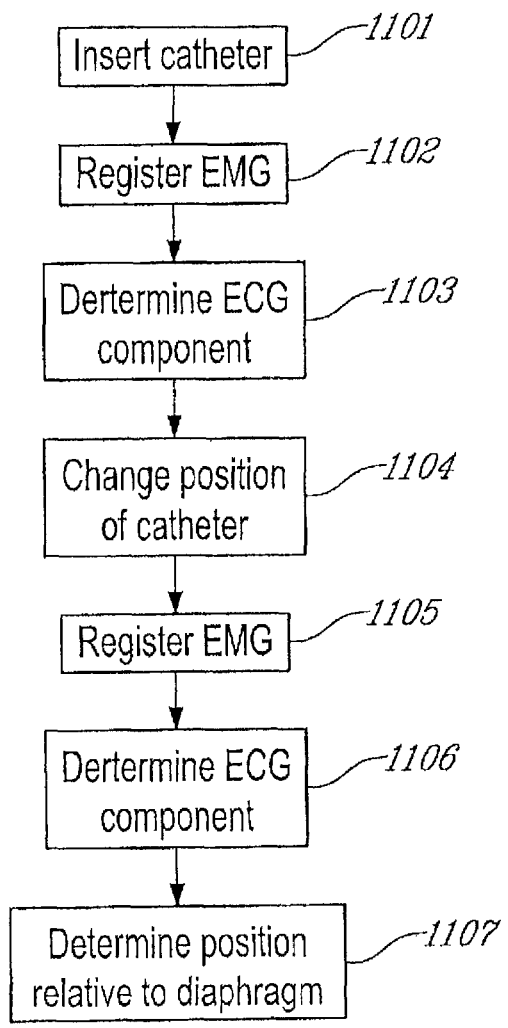
FIG. 11 is a flowchart of a method for determining the position of the esophageal catheter relative to the diaphragm.

FIG. 11 proposes a more elaborated method of optimizing the positioning of the linear array or electrodes 10 relative to the patient's diaphragm.

Step 1101: Insert the catheter. To assist in inserting the catheter, an approximate positioning method may be used, for example using NEX as described in the foregoing description. Alternatively, the depth may be estimated based on experience. The catheter is advantageously first inserted a bit less deep than the measured or estimated depth.

Step 1102: Register the bioelectric signals (EAdi signals) detected by each of the pairs of electrodes 10. These EAdi signals will comprise an ECG signal component.

Step 1103: Determine the ECG signal component of the EAdi signal detected by each of the pairs of electrodes 10.

Step 1104: Change the position of the esophageal catheter 11. If the catheter was inserted to less that the estimated depth in step 1101, this involves inserting the esophageal catheter 11 a bit deeper, for example, a distance corresponding to the distance between two pairs of electrodes 10, or twice that distance, deeper into the patient's oesophagus.

Step 1105: Register the EAdi signals detected by each of the pairs of electrodes 10. These EAdi signals will comprise an ECG signal component.

Step 1106: Determine the ECG signal component in the EAdi signals detected by each of the pairs of electrodes 10.

Steps 1105 and 1106 may be repeated as many times as required or desired for different positions of the linear array or electrodes 10 on the esophageal catheter 11, to produce different signals for comparison.

Step 1107: When at least two sets of ECG signals have been determined the position of the linear array or electrodes 10 relative to the diaphragm for each of the depths can be determined. Based on this an appropriate location of the linear array or electrodes 10 on the distal end section of the esophageal catheter 11 can be achieved.

Figure 12:
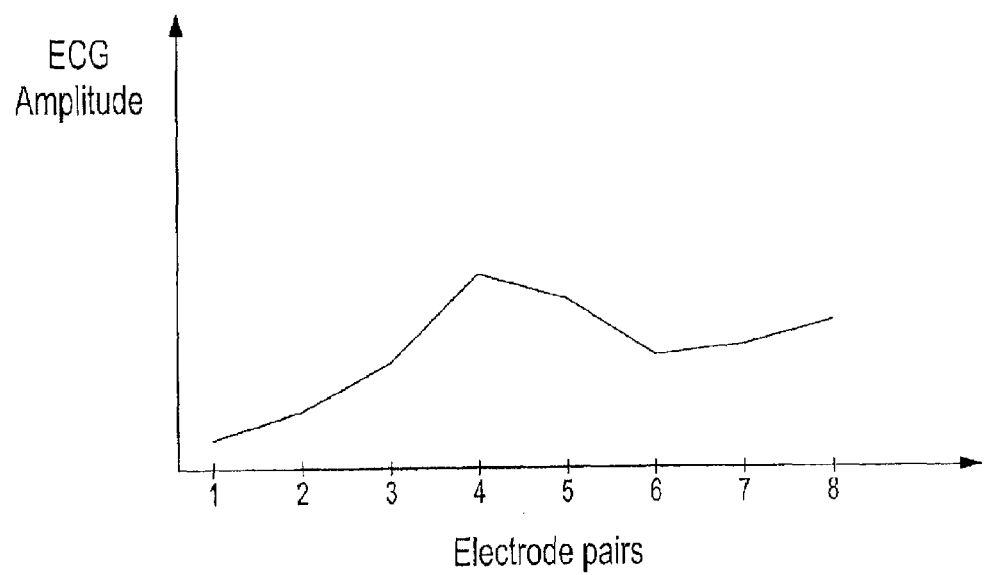
FIG. 12 is a graph illustrating an example of a user interface for displaying information related to positioning of the array of electrodes.

The result of the comparison of the ECG signal amplitudes from the different pairs of electrodes 10 may be presented to the operator in any suitable way, for example as shown in the graph of FIG. 12. FIG. 12 is essentially a two-dimensional representation of a curve similar to the one shown in FIG. 10, intended solely as an example.

As in FIG. 10, the positions of the eight pairs 1-8 of electrodes 10 are marked along the X-axis, 1 being the first electrode pair inserted into the patient and 8 being the uppermost electrode pair. The Y-axis represents the amplitude of the ECG signal component for each electrode pair. As can be seen the difference between the ECG amplitudes recorded by adjacent electrode pairs, that is the damping of the ECG signal between adjacent electrode pairs, varies. In this example, the largest difference is found between electrode pairs 3 and 4, which means that the diaphragm is located between electrode pairs 3 and 4 in this particular case. Typically, immediately above the diaphragm the ECG component will drop again.

This method may be combined with several conditions. For example, a requirement may be that the ECG amplitude is lower for the electrode pairs having lower numbers than for the electrode pairs having higher numbers. A minimum level for the difference may be set to ensure that the difference is actually caused by the damping caused by the diaphragm and not merely by, for example, the increasing distance from the heart.

It is also possible to filter out the P-wave before processing the ECG signal to ensure that the ECG signal amplitude registered is actually the amplitude of the QRS wave. How to filter out the P-wave is well known to those of ordinary skill in the art.

Figure 8:
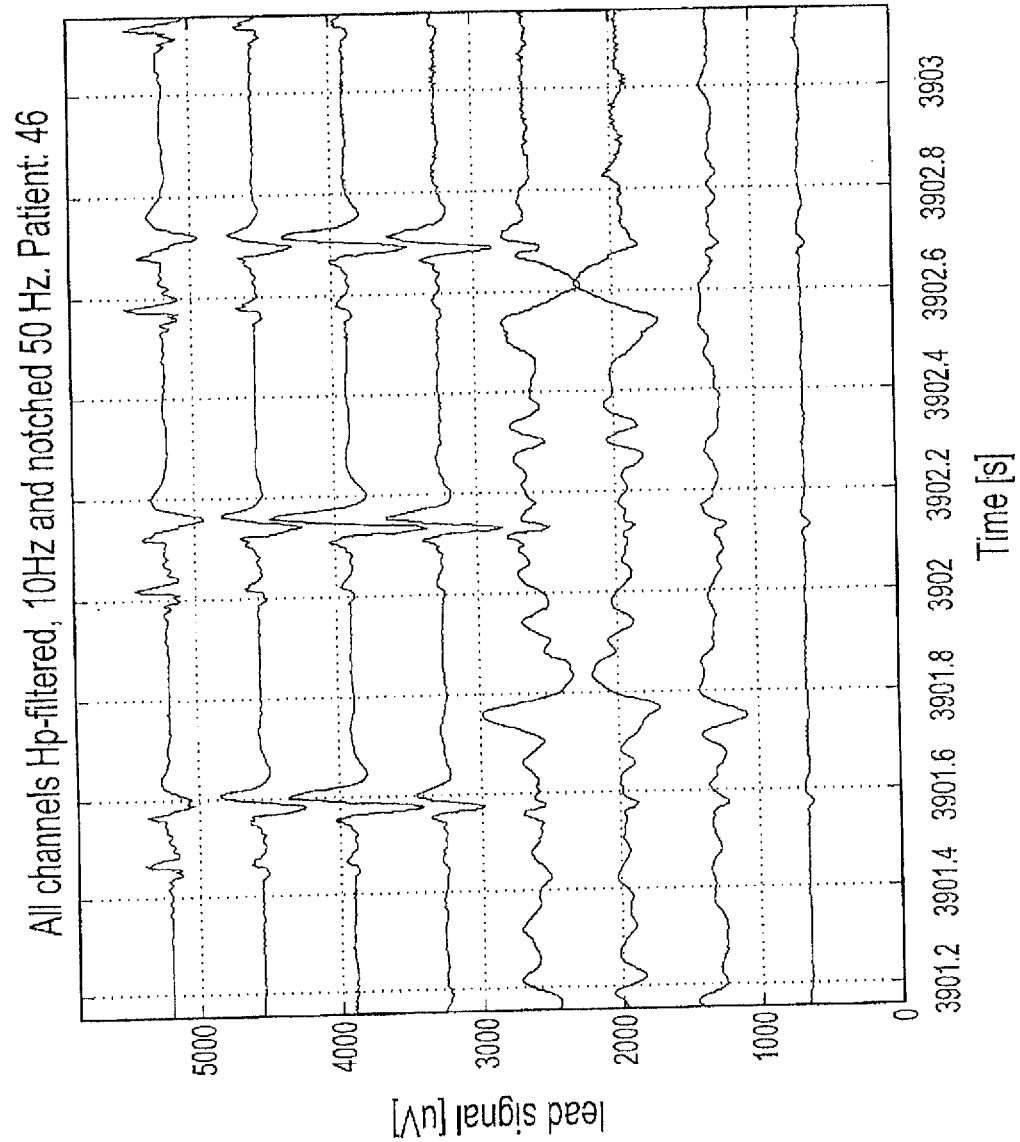
FIG. 8 is a first graph showing lower esophageal sphincter (LES) activity in EAdi signals.
Figure 9:
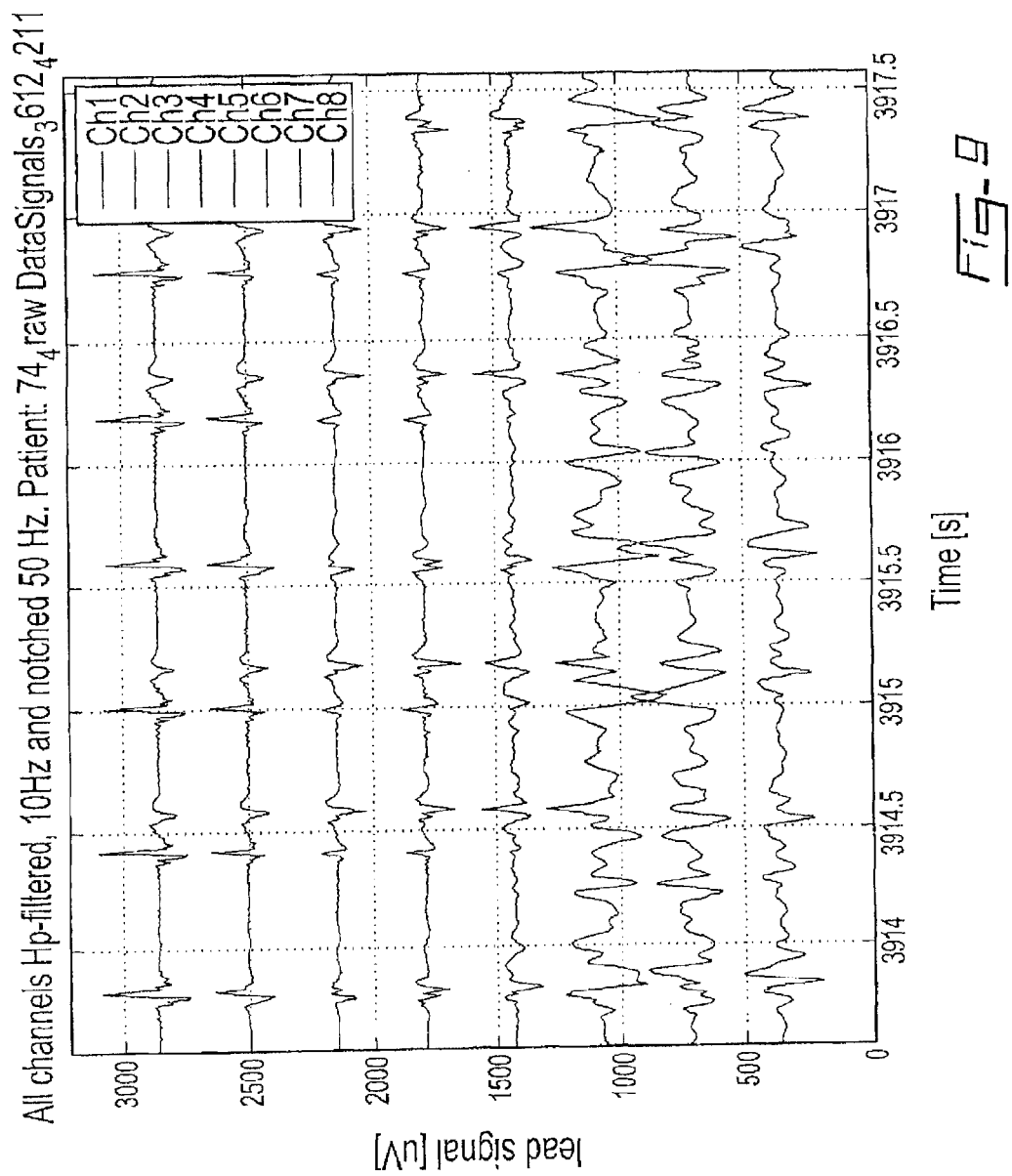
FIG. 9 is a graph showing LES activity in EAdi signals.

Lower Esophageal Sphincter (LES) Activity Verification of Electrode Array Position The lower esophageal sphincter (LES) constitutes a narrow smooth muscle band of the esophagus positioned at or just below the level where the esophagus passes though the diaphragm. Hence, LES activity also constitutes a source of crosstalk to the EADdi signals 12. Signal components having slow waveforms and high amplitude and likely related to the LES are typically caught by pairs of electrodes 10 immediately below the diaphragm in the region where the LES is expected to be located. These LES signal components are typically occurring intermittently. Examples are presented in FIGS. 8 and 9 for a number of eight (8) EAdi signals captured by a linear array of nine (9) electrodes forming eight (8) pairs of electrodes. Due to the local source of the LES, the LES signal components will, due to the configuration of the linear array of electrodes 10 shown in FIGS. 1 and 2, appear with opposite polarities above and below the LES in a manner similar to the EAdi signals 12 of FIGS. 1 and 2.

Naturally, a visual inspection of the EAdi signals 12 of FIGS. 1 and 2 can be used to detect and evaluate the amplitude and other characteristics of the LES signal components.

Figure 4:
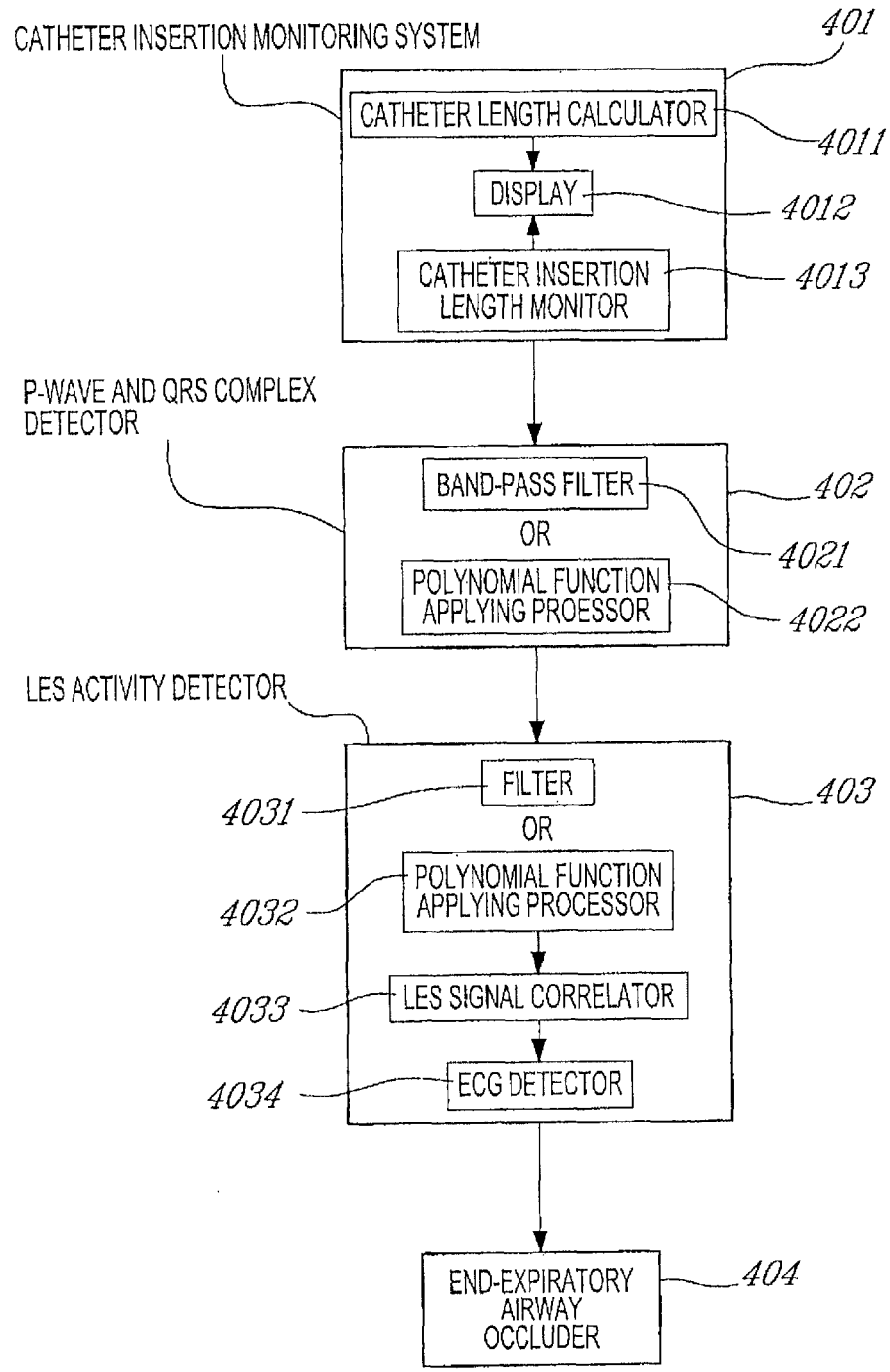
FIG. 4 is a block diagram of a non-restrictive illustrative embodiment of the device according to the invention, for positioning a linear array of electrodes in a patient's respiratory airways at the level of the patient's diaphragm.

However it is also possible to automatically determine the position and/or the presence of LES activity through a LES activity detector 403 (FIG. 4).

Due to the inverse polarity of two adjacent channels, a cross-correlation algorithm can be used to determine the location of the LES signal components. Also, since the LES waveform is very slow, the significantly higher frequencies of the EAdi signals can be removed through appropriate filtering or by applying a polynomial function.

In operation 311, the LES activity detector 403 comprises a low pass or band-pass filter 4031 to filter the EAdi signals 12 to remove the significantly higher frequencies of the EAdi signal components and thereby isolate the LES signal components. This prevents the EAdi signal components to affect the subsequent correlation to determine LES position. Alternatively, the LES activity detector 403 may comprises a processor 4032 for applying a polynomial function to the EAdi signals 12 in order to enhance the LES signal components and again prevent the EAdi signal components to affect the subsequent correlation to determine LES position.

Since the remaining signal from operation 311 is mostly representative of the LES signal components, the LES activity detector 403 comprises a correlator 4033 (not shown) of the remaining signals from adjacent channels (electrode pairs 1-7) with interruption during ECG detections (operation 312). Alternatively, the LES activity detector 403 may comprise a detector 4034 of ECG signal components that replace the detected ECG signal components by zero padding to prevent theses ECG signal components to interfere with the correlation. Obtaining during operation 312 a negative strong correlation suggests that the lower sphincter is active and if this negative strong correlation is located at or just below the channels (electrode pairs) indicating the position of the EARdi center (FIG. 2), this confirms in operation 313 adequate positioning of the array or electrodes 10. In operation 313, detection of LES activity at or below the channels (electrode pairs) where the P-waves disappear can also be used to confirm adequate positioning of the array of electrodes 10.

Hence, a third landmark for adequate positioning of the array of electrodes 10 at the level of the patient's diaphragm is derived by ensuring that LES activity occurs in the immediate proximity, i.e. at or just below the electrode pairs that indicates the location of the EARdi center, for example electrode pairs 3-5 in the example of FIG. 2.

Therefore, the LES activity detector 403 also enables monitoring of LES activity.

Verification that Electrode Array Signal Does Not Contain Expiratory Muscle Signals.

The diaphragm is an inspiratory muscle and hence effective for controlling inspiratory assist. Given a route starting in the mouth, passing through the esophagus and ending in the stomach, the position of the diaphragm is below the upper respiratory airways and above the stomach. The upper respiratory airways can generate phasic activity which can be in phase with either inspiration or expiration or both. If the electrodes 10 are located in the stomach they can potentially detect the EAdi signals from below the diaphragm, or detect expiratory muscle activity from the abdominal muscles if active.

Hence, as a final precaution, an end-expiratory occlusion of the upper respiratory airways can be performed to verify that the EAdi activity coincides with a negative deflection of the airway pressure measured by the ventilator.

For that purpose, an end-expiratory airway occluder 404 (FIG. 4) can be used to perform an automatic end-expiratory occlusion of the upper airways when the prior operations have not confirmed adequate positioning of the array of electrodes 10. The end-expiratory airway occluder 404 then verifies that the EAdi activity coincides with a negative deflection of the upper airway pressure for example as measured by the ventilator. To continuously confirm adequate positioning of the array of electrodes 10, the end-expiratory airway occluder 404 can automatically initiate the end-expiratory occlusion at given time intervals.

This fourth landmark ensures that signals antagonistic to inspiration are not measured.

When any of the above three (3) ECG, LES and expiratory muscle verifications did not confirm adequate positioning of the linear array of electrodes 10, the position of the linear array of electrodes 10 is corrected by either pulling and/or further inserting the esophageal catheter 11. After this positional correction, the above three (3) ECG, LES and expiratory muscle verifications are repeated to confirm adequate positioning of the linear array of electrodes 10 in the patient's respiratory airways at the level of the patient's diaphragm.

Specific Influence of Each of the First, Second, Third and Fourth Steps

Anatomical measurements have traditionally been used to insert nasogastric catheters for feeding purposes. However, using only this method catheters are frequently placed into the lung instead of the stomach, which induces a severe risk for the patient's health. Also, the catheter is often not placed adequately in the stomach. This has lead to the development of different means to verify accurate positioning of catheters in the stomach using air infusion or suction of fluid and pH measurements. Neither of these verification methods have been shown fully reliable. It has been found that to adequately position the linear array of electrodes 10 at the level where the esophagus passes through the diaphragm using existing anatomical measurements is unreliable when this technique alone is used.

Although the first step uses the above described regression coefficients to predict the insertion distance clearly improves the probability that the linear array of electrodes is appropriately positioned, this first step alone cannot ensure that the linear array of electrodes 10 actually has arrived in the position where the esophagus is passing through the diaphragm (e.g. the esophageal catheter 11 can fold, curl, or get into the lungs).

The second step of using the ECG can confirm that the esophageal catheter 11 is adequately positioned. In most patients, this step could be used by itself to detect adequate positioning of the linear array of electrodes 10. However, in several patients, cardiac anomalies, pathologies and/or arrhythmias prevents reliable detection of adequate electrode array positioning based on ECG only.

If the appropriate ECG pattern occurs and coincides with anatomy based prediction of the insertion distance, this certainly strengthens the probability that the linear array of electrode 10 is adequately positioned at the level of the patient's diaphragm. However, experimental evidence has indicated that this cannot ensure that the catheter has not been inserted into a lung.

If the appropriate ECG pattern occurs and coincides with EAdi signals (detected by the pairs 1-7 of electrodes 10), this certainly strengthens the probability that the electrode array is in adequate position, and excludes the possibility that the esophageal catheter 11 has penetrated one lung. If the length of insertion of the esophageal catheter 11 conforms with the length pre-calculated in response to the anatomical measurements, this further strengthens the probability of adequate positioning of the linear array of electrodes 10.

The third step consisting of using the LES activity can also confirm that the esophageal catheter 11 has been appropriately positioned. Similar to ECG, in many cases this method could be used by itself to determine the position where the electrode array should be positioned. However, LES activity is often intermittent and thus not always present at the time of catheter insertion such that reliable electrode array positioning cannot always be based on LES activity alone.

If the LES activity is present and coincides with anatomy based prediction of the catheter insertion length, this certainly strengthens the probability that the electrode array is adequately positioned. Also, it is very unlikely that the esophageal catheter 11 has been passed into a lung.

If the LES activity is present at or immediately below the channels (pairs of electrodes 10) associated with detection of the EARdi center, this certainly strengthens the probability that the array of electrodes 10 is adequately positioned. This also excludes the possibility that the esophageal catheter 11 is located in one lung. If the length of insertion of the esophageal catheter 11 conforms to the length pre-calculated in relation to anatomical measurement, this further strengthens the probability that the array of electrodes 10 os adequately positioned.

The fourth step consisting of performing an occlusion can confirm that inspiratory activity is associated with inspiratory pressure generation. However, this step cannot verify if the linear array of electrodes 10 actually has been positioned at the level where the esophagus passes through the diaphragm.

Also, the fourth step is not applicable if the patient is not breathing or if the patient is paralyzed. In contrast, the first, second and third steps are not dependent on breathing and also not affected by paralysis such that they allow detection of adequate electrode positioning even in patients who are not breathing or are paralyzed.

Naturally, removal of one of the above described steps weakens the probability of detecting adequate positioning of the array of electrodes 10 mounted on the distal end section of the esophageal catheter 11. However, the sub-combinations still have value.

As a minimum for initial positioning, the anatomical prediction should be confirmed by either ECG or LES activity. If NAVA is applied (i.e. EAdi signals are present) an occlusion should be performed to ensure that inspiratory muscles are measured.

It is to be understood that the invention is not limited in its application to the details of construction and parts illustrated in the accompanying drawings and described hereinabove. The invention is capable of other embodiments and of being practiced in various ways. It is also to be understood that the phraseology or terminology used herein is for the purpose of description and not limitation. Hence, although the present invention has been described hereinabove by way of non-restrictive illustrative embodiments thereof, these embodiments can be modified at will within the scope of the appended claims without departing from the spirit and nature of the subject invention.

REFERENCES

[1] Allo, J. C., Beck, J. C., Brander, L., Brunet, F., Slutsky, A. S., & Sinderby, C. A. (2006). Influence of neurally adjusted ventilatory assist and positive end-expiratory pressure on breathing pattern in rabbits with acute lung injury. *Crit Care Med* 34, 2997-3004.

[2] Beck, J., Campoccia, F., Allo, J. C., Brander, L., Brunet, F., Slutsky, A. S., & Sinderby, C. (2007). Improved Synchrony and Respiratory Unloading by Neurally Adjusted Ventilatory Assist (NAVA) in Lung-Injured Rabbits. *Pediatric Research* 61, 289-294.

[3] Beck, J., Sinderby, C., Lindstrom, L., & Grassino, A. (1996). Influence of bipolar esophageal electrode positioning on measurements of human crural diaphragm electromyogram. *J Appl Physiol* 81, 1434-1449.

[4] Sinderby, C., Beck, J., Spahija, J., de Marchie, M., Lacroix, J., Navalesi, P., & Slutsky, A. S. (2007). Inspiratory unloading by neurally adjusted ventilatory assist during maximal inspiratory efforts in healthy subjects. *Chest* 131, 711-717.

[5] Sinderby, C., Navalesi, P., Beck, J., Skrobik, Y., Comtois, N., Friberg, S., Gottfried, S. B., & Lindstrom, L. (1999). Neural control of mechanical ventilation in respiratory failure. *Nat. Med* 5, 1433-1436.

[6] Sinderby, C. A., Beck, J. C., Lindstrom, L. H., & Grassino, A. E. (1997). Enhancement of signal quality in esophageal recordings of diaphragm EMG. *J Appl Physiol* 82, 1370-1377.

What is claimed is:

1. A method for positioning a linear array of electrodes mounted on a distal end section of an elongated flexible member in a patient's respiratory airways at the level of the patient's diaphragm, comprising:

inserting through the patient's respiratory airways a length of the elongated flexible member pre-determined to position the linear array of electrodes at the level of the patient's diaphragm;

detecting through the electrodes of the linear array signals representative of an electrical activity of the patient's diaphragm (EAdi);

detecting ECG signal components in the EAdi signals; and detecting a correct positioning of the linear array of electrodes in the patient's respiratory airways in response to a presence, in the EAdi signals detected by the electrodes of the linear array, of an ECG signal pattern comprising ECG signal components of a first amplitude detected by distal electrode pairs of the linear array and ECG signal components of a second amplitude, greater than the first amplitude by at least a predetermined difference, detected by proximal electrode pairs of the linear array.

2. A method for positioning a linear array of electrodes as defined in claim 1, further comprising correcting the position of the linear array of electrodes if the detected position of the linear array of electrodes is inadequate.

3. A method for positioning a linear array of electrodes as defined in claim 1, further comprising:
   performing anatomical measurements; and
   determining the pre-determined length of the elongated flexible member as a function of the anatomical measurements.

4. A method for positioning a linear array of electrodes as defined in claim 3, wherein performing anatomical measurements comprises measuring a nose-to-ear-to-xiphoid distance and wherein the pre-determined length is calculated by multiplying the nose-to-ear-to-xiphoid distance by a regression coefficient.

5. A method for positioning a linear array of electrodes as defined in claim 4, comprising determining the regression coefficient as a function of an indication as to whether the elongated flexible member will be inserted through the mouth or through a nostril.

6. A method for positioning a linear array of electrodes as defined in claim 1, wherein inserting through the patient's respiratory airways a pre-determined length of the elongated flexible member comprises:
   monitoring a length of the elongated flexible member having been inserted through the patient's respiratory airways; and
   stopping insertion of the elongated flexible member through the patient's respiratory airways when the monitored length has reached the pre-determined length.

7. A method for positioning a linear array of electrodes as defined in claim 6, comprising monitoring the length of the elongated flexible member having been inserted through the patient's respiratory airways from a center of the linear array of electrodes.

8. A method for positioning a linear array of electrodes as defined in claim 6, comprising displaying, upon insertion of the elongated flexible member through the patient's respiratory airways, the pre-determined length and the monitored length.

9. A method for positioning a linear array of electrodes as defined in claim 1, wherein the elongated flexible member is an esophageal catheter.

10. A method for positioning a linear array of electrodes mounted on a distal end section of an elongated flexible member in a patient's respiratory airways at the level of the patient's diaphragm, comprising:
   inserting through the patient's respiratory airways a length of the elongated flexible member predetermined to position the linear array of electrodes at the level of the patient's diaphragm;
   detecting through the electrodes of the linear array signals representative of an electrical activity of the patient's diaphragm (EAdi);
   detecting ECG signal components in the EAdi signals; and
   detecting the position of the linear array of electrodes in the patient's respiratory airways in response to detection of ECG signal components in the EAdi signals,
   wherein detecting the ECG signal components in the EAdi signals comprises detecting in the EAdi signals a presence or absence of a P-wave of the patient's ECG.

11. A method for positioning a linear array of electrodes as defined in claim 10, wherein detecting in the EAdi signals the presence or absence of a P-wave of the patient's ECG comprises filtering the EAdi signals to enhance the ECG signal components while attenuating EAdi signal components.

12. A method for positioning a linear array of electrodes as defined in claim 10, wherein detecting in the EAdi signals the presence or absence of a P-wave of the patient's ECG comprises applying to the EAdi signals a polynomial function to enhance the ECG signal components while attenuating EAdi signal components.

13. A method for positioning a linear array of electrodes as defined in claim 10, wherein:
   the linear array of electrodes comprises a plurality of pairs of electrodes to produce the EAdi signals, the method further comprising:
   detecting a presence of a QRS complex in all the EAdi signals upon detecting ECG components in the EAdi signals of all the pairs of electrodes simultaneously.

14. A method for positioning a linear array of electrodes as defined in claim 10, wherein:
   the linear array of electrodes comprises a plurality of pairs of electrodes to produce the EAdi signals; and
   detecting in the EAdi signals the presence or absence of a P-wave of the patient's ECG comprises indicating the presence of a P-wave in the EAdi signals produced by proximal pairs of electrodes upon detecting in the EAdi signals produced by said proximal pairs a QRS complex preceded within a given period of time by an amplitude appearing only on said proximal pairs of electrodes.

15. A method for positioning a linear array of electrodes as defined in claim 10, wherein:
   the linear array of electrodes comprises a plurality of pairs of electrodes to produce the EAdi signals; and
   detecting the position of the linear array of electrodes comprises detecting adequate positioning of the linear array of electrodes upon detecting the presence of a P-wave in the EAdi signals produced by proximal pairs of electrodes, detecting the absence of a P-wave in the EAdi signals produced by distal pairs of electrodes, and detecting a presence of a QRS complex in the EAdi signals produced by all the pairs of electrodes.

16. A method for positioning a linear array of electrodes mounted on a distal end section of an elongated flexible member in a patient's respiratory airways at the level of the patient's diaphragm, comprising:
   inserting through the patient's respiratory airways a length of the elongated flexible member predetermined to position the linear array of electrodes at the level of the patient's diaphragm;
   detecting through the electrodes of the linear array signals representative of an electrical activity of the patient's diaphragm (EAdi);
   detecting ECG signal components in the EAdi signals;
   detecting the position of the linear array of electrodes in the patient's respiratory airways in response to detection of ECG signal components in the EAdi signal;
   performing an end-expiratory occlusion of the patient's respiratory airways;
   verifying during the end-expiratory occlusion that the electrical activity of the diaphragm coincides with a negative deflection of the patient's respiratory airways pressure; and
   detecting adequate positioning of the linear array of electrodes in the patient's respiratory airways when the electrical activity of the diaphragm coincides with a negative deflection of the patient's respiratory airways pressure during the end-expiratory occlusion.

17. A method for positioning a linear array of electrodes as defined in claim 16, comprising initiating an end-expiratory occlusion of the patient's respiratory airways at given time intervals.

18. A device for positioning a linear array of electrodes mounted on a distal end section of an elongated flexible member in a patient's respiratory airways at the level of the patient's diaphragm, wherein a length of the elongated flexible member pre-determined to position the linear array of electrodes at the level of the patient's diaphragm is first inserted through the patient's respiratory airways and wherein the device comprises:

means for detecting through the electrodes of the linear array signals representative of an electrical activity of the patient's diaphragm (EAdi);

means for detecting ECG signal components in the EAdi signals; and means for detecting a correct positioning of the linear array of electrodes in the patient's respiratory airways in response to a presence, in the EAdi signals detected by the electrodes of the linear array, of an ECG signal pattern comprising ECG signal components of a first amplitude detected by distal electrode pairs of the linear array and ECG signal components of a second amplitude, greater than the first amplitude by at least a predetermined difference, detected by proximal electrode pairs of the linear array.

19. A device for positioning a linear array of electrodes mounted on a distal end section of an elongated flexible member in a patient's respiratory airways at the level of the patient's diaphragm, wherein a length of the elongated flexible member pre-determined to position the linear array of electrodes at the level of the patient's diaphragm is first inserted through the patient's respiratory airways and wherein the device comprises:

a first detector of signals representative of an electrical activity of the patient's diaphragm (EAdi) through the electrodes of the linear array;

a second detector of ECG signal components in the EAdi signals; and a third detector of a correct positioning of the linear array of electrodes in the patient's respiratory airways in response to a presence, in the EAdi signals detected by the electrodes of the linear array, of an ECG signal pattern comprising ECG signal components of a first amplitude detected by distal electrode pairs of the linear array and ECG signal components of a second amplitude, greater than the first amplitude by at least a predetermined difference, detected by proximal electrode pairs of the linear array.

20. A device for positioning a linear array of electrodes as defined in claim 19, comprising a monitor of the insertion through the patient's respiratory airways of the pre-determined length of the elongated flexible member to position the linear array of electrodes at the level of the patient's diaphragm.

21. A device for positioning a linear array of electrodes as defined in claim 20, wherein the monitor comprises a calculator of the pre-determined length of the elongated flexible member as a function of anatomical measurements.

22. A device for positioning a linear array of electrodes as defined in claim 21, wherein the anatomical measurements comprise a nose-to-ear-to-xiphoid distance measurement, and wherein the calculator of the pre-determined length multiplies the nose-to-ear-to-xiphoid distance by a regression coefficient.

23. A device for positioning a linear array of electrodes as defined in claim 22, wherein the calculator of the monitor determines the value of the regression coefficient in response to an indication as to whether the elongated flexible member will be introduced through the mouth or a nostril.

24. A device for positioning a linear array of electrodes as defined in claim 20, wherein the monitor comprises a fourth detector for measuring a length of the elongated flexible member having been inserted through the patient's respiratory airways, wherein insertion of the elongated flexible member through the patient's respiratory airways is stopped when the monitored length has reached the pre-determined length.

25. A device for positioning a linear array of electrodes as defined in claim 24, wherein the fourth detector measures the length of the elongated flexible member from the center of the linear array of electrodes.

26. A device for positioning a linear array of electrodes as defined in claim 24, wherein the monitor comprises a display for displaying, upon insertion of the elongated flexible member through the patient's respiratory airways, the pre-determined length and the measured length.

27. A device for positioning a linear array of electrodes as defined in claim 19, wherein the elongated flexible member is an esophageal catheter.

28. A device for positioning a linear array of electrodes mounted on a distal end section of an elongated flexible member in a patient's respiratory airways at the level of the patient's diaphragm, wherein a length of the elongated flexible member predetermined to position the linear array of electrodes at the level of the patient's diaphragm is first inserted through the patient's respiratory airways, the device comprising:

a first detector of signals representative of an electrical activity of the patient's diaphragm (EAdi) through the electrodes of the linear array;

a second detector of ECG signal components in the EAdi signals; and a third detector of the position of the linear array of electrodes in the patient's respiratory airways in response to the detected ECG signal components in the EAdi signals, wherein the second detector detects the ECG signal components by detecting in the EAdi signals a presence or absence of a P-wave of the patient's ECG.

29. A device for positioning a linear array of electrodes as defined in claim 28, wherein the second detector comprises a filter for filtering the EAdi signals to enhance the ECG signal components while attenuating EAdi signal components.

30. A device for positioning a linear array of electrodes as defined in claim 28, wherein the second detector comprises a processor for applying to the EAdi signals a polynomial function to enhance the ECG signal components while attenuating EAdi signal components.

31. A device for positioning a linear array of electrodes as defined in claim 28, wherein:

the linear array of electrodes comprises a plurality of pairs of electrodes to produce the EAdi signals; and the second detector indicates a presence of a QRS complex in all the EAdi signals upon detecting ECG components in the EAdi signals produced on all the pairs of electrodes simultaneously.

32. A device for positioning a linear array of electrodes as defined in claim 28, wherein:

the linear array of electrodes comprises a plurality of pairs of electrodes to produce the EAdi signals; and the second detector indicates the presence of a P-wave in the EAdi signals produced by proximal pairs of electrodes upon detecting in the EAdi signals produced by said proximal pairs a QRS complex preceded within a given period of time by an amplitude appearing only on said proximal pairs of electrodes.

33. A device for positioning a linear array of electrodes as defined in claim 28, wherein:

the linear array of electrodes comprises a plurality of pairs of electrodes to produce the EAdi signals; and the device further comprises an indicator of adequate positioning of the linear array of electrodes upon detection of the presence of a P-wave in the EAdi signals produced by proximal pairs of electrodes, detecting the absence of a P-wave in the EAdi signals produced by distal pairs of electrodes, and detecting a presence of a QRS complex in the EAdi signals produced by all the pairs of electrodes.

34. A device for positioning a linear array of electrodes mounted on a distal end section of an elongated flexible member in a patient's respiratory airways at the level of the patient's diaphragm, wherein a length of the elongated flexible member predetermined to position the linear array of electrodes at the level of the patient's diaphragm is first inserted through the patient's respiratory airways, comprising

- a first detector of signals representative of an electrical activity of the patient's diaphragm (EAdi) through the electrodes of the linear array;
- a second detector of ECG signal components in the EAdi signals;
- a third detector of the position of the linear array of electrodes in the patient's respiratory airways in response to the detected ECG signal components in the EAdi signals; and
- an end-expiratory airway occluder for performing an end-expiratory occlusion of the patient's respiratory airways,
- wherein the end-expiratory airway occluder (a) verifies during the end-expiratory occlusion that the electrical activity of the diaphragm coincides with a negative deflection of the patient's respiratory airways pressure and (b) detects adequate positioning of the linear array of electrodes in the patient's respiratory airways when the electrical activity of the diaphragm coincides with a negative deflection of the patient's respiratory airways pressure during the end-expiratory occlusion.

35. A device for positioning a linear array of electrodes as defined in claim 34, wherein the end-expiratory airway occluder initiates an end-expiratory occlusion of the patient's respiratory airways at given time intervals.

* * * * *